United States Patent
Mutel et al.

(10) Patent No.: US 6,284,785 B1
(45) Date of Patent: Sep. 4, 2001

(54) 1-ARENESULFONYL-2-ARYL-PYRROLIDINE AND PYRIDINE DERIVATIVES

(75) Inventors: Vincent Mutel, Mulhouse (FR); Eric Vieira, Allschwil (CH); Jürgen Wichmann, Steinen (DE)

(73) Assignee: Hoffmann- La Roche Inc., Nutley, NJ (US)

( * ) Notice: Subject to any disclaimer, the term of this patent is extended or adjusted under 35 U.S.C. 154(b) by 0 days.

(21) Appl. No.: 09/534,380

(22) Filed: Mar. 24, 2000

(30) Foreign Application Priority Data

Mar. 25, 1999 (EP) .................................................. 99106004

(51) Int. Cl.[7] ................ A61K 31/4025; A61K 31/4439; C07D 207/48; C07D 401/04; A61P 9/10
(52) U.S. Cl. .......................... 514/424; 514/343; 514/428; 514/429; 514/444; 514/461; 544/141; 546/278.4; 548/517; 548/518; 548/527; 548/542; 549/59; 549/472
(58) Field of Search ..................... 514/343, 424; 546/278.4; 548/542

(56) References Cited

U.S. PATENT DOCUMENTS 5,296,494 * 3/1994 Lavielle et al. ..................... 514/343

FOREIGN PATENT DOCUMENTS 549 407A 6/1993 (EP) .
97/48681 12/1997 (WO) .

OTHER PUBLICATIONS

Carl R. Noller, Chemistry of Organic Compounds, W.B. Saunders Company, Philadelphia, PA (1965);pp. 508–509.*
Schlaeger et al., *New Dev. New Appl. Anim.Cell Techn. Proc. ESACT Meeting*, pp. 105–112 and 117–120 (1998).

G. Kresze et al., *Liebigs. Ann. Chem.*, vol. 762, pp. 93–105 (1972).

Tamaru et al., *J. Org.Chem.*, vol. 51, pp. 4089–4090 (1986).

Pal et al., A General Stereocontrolled Synthesis of cis–2,3 Disubstituted Pyrrolidines and Piperidines, Tetrahedron Letters, vol. 34, No. 39, pp. 6205–6208 (1993).

Trost et al, A[3+2] and [4+3]Cycloaddition Approach to N–Heterocycles via Pd–Catalyzed TMM Reactions with Imines, J. Am. Chem. Soc., vol. 115, pp. 6636–6645 (1993).

* cited by examiner

Primary Examiner—Jane C. Oswecki
(74) Attorney, Agent, or Firm—George W. Johnston; William H. Epstein; Arthur D. Dawson

(57) ABSTRACT

1-Arenesulfonyl-2-Aryl-pyrrolidine and pyridine derivatives having activity as ligands of metabotropic glutamate receptors of the formula

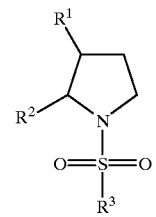

are disclosed.

44 Claims, No Drawings

1-ARENESULFONYL-2-ARYL-PYRROLIDINE AND PYRIDINE DERIVATIVES

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

SUMMARY OF THE INVENTION

The present invention is concerned with 1-arenesulfonyl-2-aryl-pyrrolidine and piperidine derivatives of formula

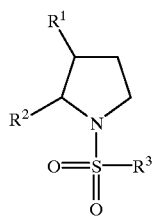

I wherein
$R^1$ signifies hydrogen, lower alkyl or hydroxy-lower alkyl;
$R^2$ signifies furyl, thienyl, pyridyl or phenyl, which is optionally substituted by 1 to 3 substituents, selected from lower alkyl, lower alkoxy, halogen, cyano, $CF_3$ or $-N(R^4)_2$;
$R^3$ signifies naphthyl or phenyl, which is optionally substituted by 1 to 3 substituents, selected from lower alkyl, lower alkoxy, halogen, acetyl, cyano, hydroxy-lower alkyl, $-CH_2$-morpholin-4-yl, lower alkyl-oxy-lower alkyl, lower alkyl-$N(R^4)_2$ or $CF_3$;
$R^4$ signifies, independently from each other, hydrogen or lower alkyl,
as well as their pharmaceutically acceptable salts.

Compounds of formula I are novel with the exception of (RS)-2-phenyl-1-(toluene-4-sulfonyl)-pyrrolidine and (RS)-1-(toluene-4-sulfonyl)-2-p-tolyl-pyrrolidine. The manufacture of these compounds is described in J. Org. Chem., 51, (1986) 4089–4090. Furthermore, the preparation of (RS)-2-phenyl-1-(toluene-4-sulfonyl)-pyrrolidine is described in Liebigs Ann. Chem., 762, (1972) 93–105.

It has surprisingly been found that the compounds of general formula I are metabotropic glutamate receptor modulators, acting as antagonists or agonists. Compounds of formula I are distinguished by valuable therapeutic properties.

Objects of the present invention are compounds of formula I and their pharmaceutically acceptable salts per se and as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments.

DETAILED DESCRIPTION OF THE INVENTION

Preferred compounds of formula I,

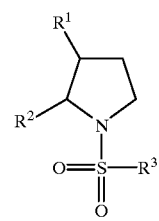

I in the scope of the present invention are those, in which
$R^1$ signifies hydrogen or methyl;
$R^2$ signifies phenyl, optionally substituted by halogen, lower alkyl, $CF_3$ or $-N(CH_3)_2$;
with the exception of (RS)-2-phenyl-1-(toluene-4-sulfonyl)-pyrrolidine and (RS)-1-(toluene-4-sulfonyl)-2-p-tolyl-pyrrolidine and their salts.

The following are examples of such compounds:
(RS)-2-(3-fluoro-phenyl)-1-(toluene-4-sulfonyl)-pyrrolidine,
(RS)-1-(4-chloro-benzenesulfonyl)-2-(3-fluoro-phenyl)-pyrrolidine,
(RS)-1-(4-chloro-benzenesulfonyl)-2-phenyl-pyrrolidine,
(RS)-2-(4-chloro-phenyl)-1-(toluene-4-sulfonyl)-pyrrolidine,
(RS)-1-(4-chloro-benzenesulfonyl)-2-(4-fluoro-phenyl)-pyrrolidine,
(RS)-2-(4-fluoro-phenyl)-1-(toluene-4-sulfonyl)-pyrrolidine,
(RS)-1-benzenesulfonyl-2-(4-chloro-phenyl)-pyrrolidine,
(RS)-1-(4-fluoro-benzenesulfonyl)-2-(4-fluoro-phenyl)-pyrrolidine, (RS)-2-(4-fluoro-phenyl)-1-(toluene-2-sulfonyl)-pyrrolidine,
(RS)-1-(4-chloro-benzenesulfonyl)-2-p-tolyl-pyrrolidine,
(RS)-1-(4-ethyl-benzenesulfonyl)-2-(4-fluoro-phenyl)-pyrrolidine,
(RS)-1-(toluene-4-sulfonyl)-2-m-tolyl-pyrrolidine,
(RS)-2-(3-chloro-phenyl)-1-(toluene-4-sulfonyl)-pyrrolidine,
(RS)-2-(3,4-difluoro-phenyl)-1-(toluene-4-sulfonyl)-pyrrolidine,
(RS)-2-(3-chloro-4-fluoro-phenyl)-1-(toluene-4-sulfonyl)-pyrrolidine,
(RS)-1-(4-fluoro-benzenesulfonyl)-2-(4-dimethylamino-3-chloro-phenyl)-pyrrolidine,
(RS)-1-(toluene-4-sulfonyl)-2-(4-trifluoromethyl-phenyl)-pyrrolidine,
(RS)-2-(4-chloro-3-methyl-phenyl)-1-(toluene-4-sulfonyl)-pyrrolidine,
(RS)-2-(4-fluoro-phenyl)-1-(4-trifluoromethyl-benzenesulfonyl)-pyrrolidine,
(RS)-2-(N,N-dimethylamino-phenyl)-1-(4-fluoro-benzenesulfonyl)-pyrrolidine,
(R)-1-(4-chloro-benzenesulfonyl)-2-(4-fluoro-phenyl)-pyrrolidine,
(S)-1-(4-chloro-benzenesulfonyl)-2-(4-fluoro-phenyl)-pyrrolidine,
(RS)-2-(4-ethyl-phenyl)-1-(toluene-4-sulfonyl)-pyrrolidine,
(RS)-2-(4-ethyl-phenyl)-1-(4-fluoro-benzenesulfonyl)-pyrrolidine,
(S)-2-(4-fluoro-phenyl)-1-(toluene-4-sulfonyl)-pyrrolidine,
(R)-2-(4-fluoro-phenyl)-1-(toluene-4-sulfonyl)-pyrrolidine,
(RS)-2-(4-fluoro-phenyl)-1-(4-methoxymethyl-benzenesulfonyl)-pyrrolidine and
(2RS,3RS)-2-(4-fluoro-phenyl)-3-methyl-1-(toluene-4-sulfonyl)-pyrrolidine Compounds of formula I, in which R$^1$ signifies hydrogen; and R$^2$ signifies furyl, thienyl or pyridyl;

are also preferred.

The following are examples of such compounds:
(RS)-1-(4-chloro-benzenesulfonyl)-2-thien-2-yl-pyrrolidine,
(RS)-2-thien-2-yl-1-(toluene-4-sulfonyl)-pyrrolidine,
(RS)-2-thien-3-yl-1-(toluene-4-sulfonyl)-pyrrolidine and
(RS)-2-furan-2-yl-1-(toluene-4-sulfonyl)-pyrrolidine.

The invention embraces all stereoisomeric forms in addition to the racemates.

Unless otherwise indicated, the following definitions are set forth to illustrate and defined the meaning and scope of the various terms used to describe the invention herein.

The term "lower alkyl" denotes straight-chain or branched saturated hydrocarbon residues with 1–7 carbon atoms, preferably with 1–4 carbon atoms, such as methyl, ethyl, n-propyl, i-propyl and the like.

The term "lower alkoxy" denotes a lower alkyl residue in the sense of the foregoing definition bonded via an oxygen atom.

The term "halogen" embraces fluorine, chlorine, bromine and iodine.

The compounds of formula I and their pharmaceutically acceptable salts can be manufactured by:

reacting a compound of the formula

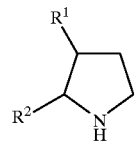

II with a compound of formula

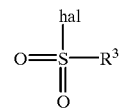

III and, if desired,
converting a functional group in a compound of formula I into another functional group and, if desired,
converting a compound of formula I into a pharmaceutically acceptable salt.

In accordance with the invention an appropriately substituted compound of formula II, for example (RS)-2-(3-fluoro-phenyl)-pyrrolidine, is reacted with a suitable compound of formula III, for example toluene-4-sulfonyl chloride. The reaction according to known methods takes place at room temperature within 16 hours in an inert solvent, for example in dichloromethane. After evaporating the solvent, the mixture is dissolved in water and extracted with a suitable solvent, for example ethyl acetate and purified using known methods.

In particular, cyano groups can be hydrogenated to amino groups or halogen atoms in halogenated lower alkyl groups can be substituted with amins or converted to ethers.

The hydrogenation is preferably effected with Raney-nickel at room temperature under normal pressure and the amino group can be alkylated by known methods.

The ether formation of benzylchloride derivatives can be conveniently carried out as follows: A compound of general formula I which contains a halogenated lower alkyl group, for example (RS)-2-(4-fluoro-phenyl)-1-(4-chloromethyl-benzenesulfonyl)-pyrrolidine is reacted with sodium methanolate in MeOH for 80 hours at 50° C. and purified using known methods.

The substitution of a halogen atom in a halogenated lower alkyl group with an amine can be conveniently carried out as follows: A compound of general formula I which contains a halogenated lower alkyl group, for example (RS)-2-(4-fluoro-phenyl)-1-(4-chloromethyl-benzenesulfonyl)-pyrrolidine is reacted with morpholine in DMF for 17 hours at 80° C. and purified using known methods.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

Scheme 1 gives an overview of the manufacture of the compounds of formula I starting from known compounds. Substituents R¹ present in the compounds of formula I are introduced according to methods known to the person skilled in the art. The manufacture of representative compounds of formula I is described in detail in examples 1–84 and 88–91.

Scheme 2 and scheme 3 giving an overview of the conversions of functional groups in compounds of formula I described in detail in examples 85–87.

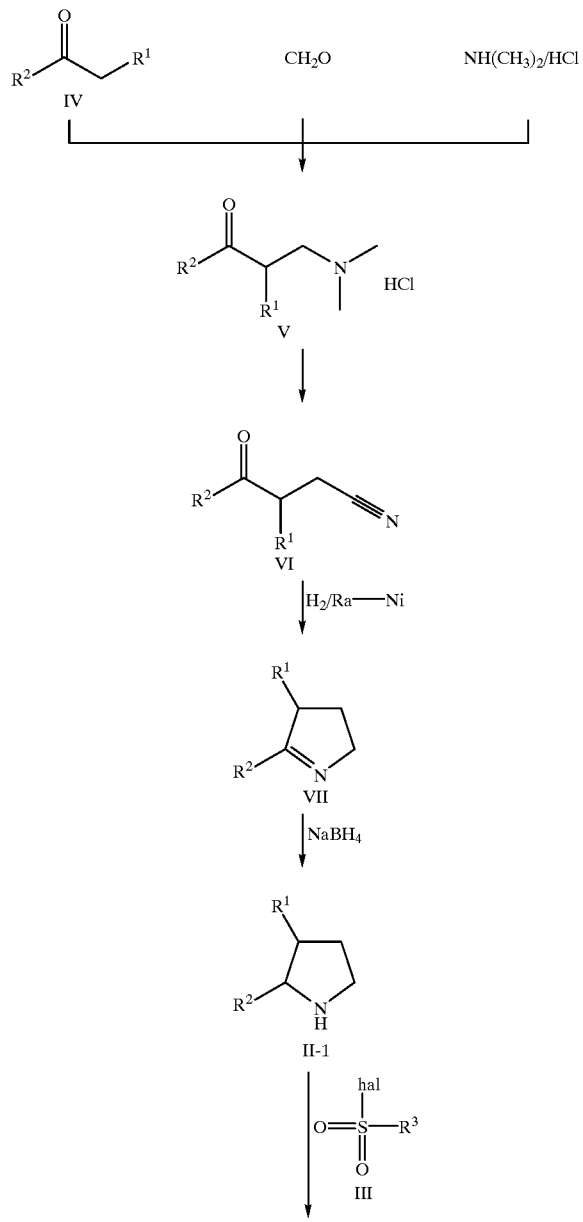

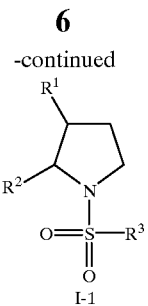

I-1

$R^1$ is hydrogen or lower alkyl and the other substituents having the significances given earlier.

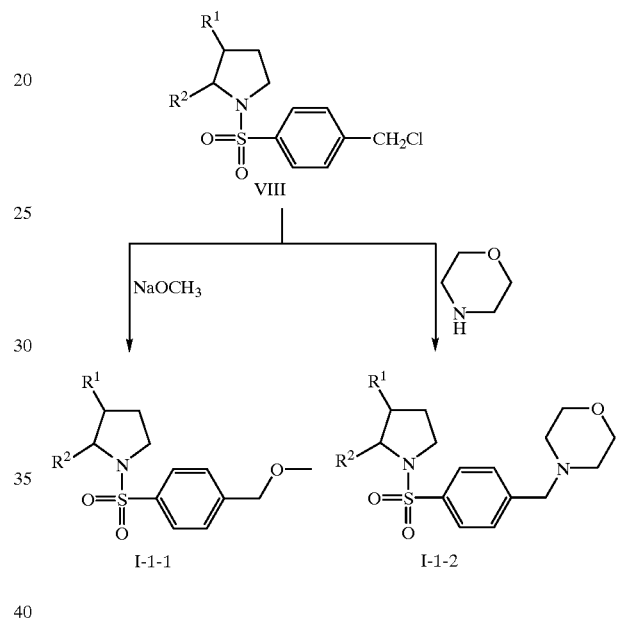

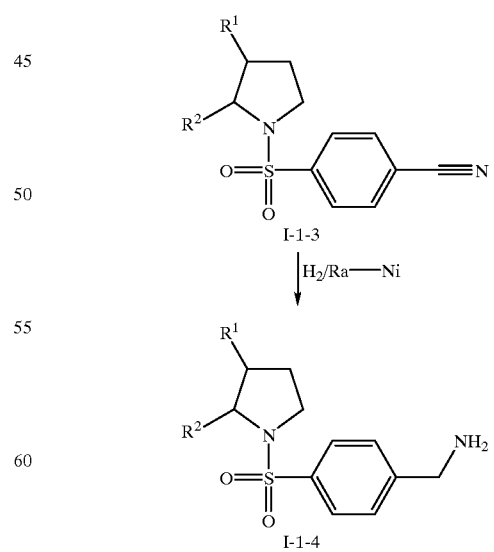

The compounds of formula I and their pharmaceutically acceptable salts are, as already mentioned above, metabotropic glutamate receptor agonists and/or antagonists and can be used for the treatment or prevention of acute and/or chronic neurological disorders, such as psychosis, schizophrenia, Alzheimer's disease, cognitive disorders and memory deficits, as well as acute and chronic pain. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGlu receptor agonists and/or antagonists. It has been shown that the compounds of examples 1–4, 6, 8, 9, 11–14, 16, 19, 21, 25, 26, 29, 31, 38, 39, 40, 48, 55, 56, 58, 60, 69, 72, 77, 78, 81, 82, 83, 84, 85, 88, 89, 90 and 91 show agonistic activty, the other specific examples have an antagonistic activity to the mGlu receptor. The compounds show activities, as measured in the assay described below, of 50 $\mu$M or less, typically 3 $\mu$M or less, and ideally of 0.5 $\mu$M or less.

In the table below are shown some specific activity-data:

| Example No. | agonist/antagonist | IC$_{50}$ ($\mu$M) |
| --- | --- | --- |
| 3 | agonist | 8.22 |
| 4 | agonist | 0.23 |
| 88 | agonist | 0.62 |
| 7 | antagonist | 8.00 |
| 18 | antagonist | 1.37 |
| 36 | antagonist | 0.56 | cDNA encoding rat mGlu 1a receptor obtained from Prof. Nakanishi (Kyoto, Japan) was transiently tranfected into EBNA cells using a procedure described by Schlaeger et. al, New Dev. New Appl. Anim Cell Techn., Proc. ESACT Meet., 15$^{th}$ (1998), 105–112 and 117–120. [Ca$^{2+}$]i measurements were performed on mGlu 1a transfected EBNA cells after incubation of the cells with Fluo-3 AM (0.5 $\mu$M final concentration) for 1hour at 37° C. followed by 4 washes with assay buffer (DMEM supplemented with Hank's salt and 20 mM HEPES. [Ca$^{2+}$]i measurements were done using a fluorometric imaging plate reader (FLIPR, Molecular Devices Corporation, La Jolla, Calif. USA). When compounds were evaluated as antagonists they were tested against 10 $\mu$M glutamate as agonist.

The inhibition (antagonists) or activation (agonists) curves were fitted with a four parameter logistic equation giving EC$_{50}$, IC$_{50}$, and Hill coefficient using the iterative non linear curve fitting software Origin (Microcal Software Inc., Northampton, Mass., USA).

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorantss, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

EXAMPLE 1

(RS)-2-(3-Fluoro-phenyl)-1-(toluene-4-sulfonyl)-pyrrolidine a) 3-Dimethylamino-1-(3-fluoro-phenyl)-propan-1-one hydrochloride (1:1)

A stirred mixture of 3-fluoro-acetophenone (10.5 g, 75.7 mmol), paraformaldehyde (3.79 g, 126 mmol), dimethylamine hydrochloride (6.17 g, 75.7 mmol), conc. HCl (0.2 ml) and ethanol (17 ml) was refluxed for 1.5 h. The clear solution was cooled to 0° C. and diethyl ether (100 ml) was added. The formed white solid was collected, washed with diethyl ether and recrystallized from EtOH/diethyl ether to yield the product (10.2 g, 58%) as a white solid, m.p. 152° C. and MS: m/e=195 (M$^+$).

b) 4-(3-Fluoro-phenyl)-4-oxo-butylronitrile

A stirred mixture of 3-dimethylamino-1-(3-fluoro-phenyl)-propan-1-one hydrochloride (5.20 g, 22.4 mmol)

and potassium cyanide (2.19 g, 33.6 mmol) was refluxed for 17 h, evaporated dissolved in water (150 ml) and extracted with ethyl acetate (2×120 ml). The combined organic layers were washed with water (120 ml), brine (120 ml), 3N sulfuric acid (100 ml) and brine (100 ml), dried (MgSO$_4$) and evaporated to give an orange oil (2.15 g) which was further purified by column chromatography on silica gel (ethyl acetate/hexane 1:3) to yield the product (1.68 g, 42%) as a pale yellow solid, m.p. 46° C. and MS: m/e=177 (M$^+$).

c) 5-(3-Fluoro-phenyl)-3,4-dihydro-2H-pyrrole 4-(3-Fluoro-phenyl)-4-oxo-butyronitrile (1.60 g, 9.03 mmol) dissolved in MeOH (45 ml) and 3.5 N MeOH-NH$_3$ (45 ml) was hydrogenated on Ra-Ni at RT for 16 h. The catalyst was filtered off, the filtrate evaporated and the crude product purified by column chromatography on silica gel (ethyl acetate/toluene 1:2) to give the product (1.16 g, 79%) as a colorless oil, MS: m/e=163 (M$^+$).

d) (RS)-2-(3-Fluoro-phenyl)-pyrrolidine

To a stirred solution of 5-(3-fluoro-phenyl)-3,4-dihydro-2H-pyrrole (1.10 g, 6.74 mmol) in methanol (40 ml) was added at 0° C. sodium borohydride (0.51 g, 13.4 mmol) and the reaction mixture was stirred at RT for 1 h. Then additional sodium borohydride (0.25 g, 6.61 mmol) was added and stirring was continued for 1 h. The mixture was evaporated, dissolved in saturated NaHCO$_3$-solution (70 ml) and extracted with dichloromethane (2×70 ml). The combined organic layers were washed with brine (70 ml), dried (MgSO$_4$) and evaporated. The crude product was purified by column chromatography on silica gel (dichloromethane/MeOH/NH$_4$OH 15:1:0.1) to give the product (0.77 g, 69%) as a colorless oil, MS: m/e=165 (M$^+$).

e) (RS)-2-(3-Fluoro-phenyl)-1-(toluene-4-sulfonyl)-pyrrolidine

To a stirred solution of (RS)-2-(3-fluoro-phenyl)-pyrrolidine (0.24 g, 1.45 mmol) and triethylamine (0.40 ml, 2.87 mmol) in dichloromethane (40 ml) was added at 0° C. toluene-4-sulfonyl chloride (0.42 g, 2.20 mmol). The mixture was stirred at RT for 16 h, evaporated, dissolved in water (40 ml) and extracted with ethyl acetate (2×40 ml). The combined organic layers were washed with water (40 ml), brine (40 ml), dried (MgSO$_4$) and evaporated. The crude product was purified by crystallization from ethyl acetate/hexane to give the product (0.38 g, 83%) as a white solid, m.p. 116° C. and MS: m/e=319 (M$^+$).

EXAMPLE 2

(RS)-1-(4-Chloro-benzenesulfonyl)-2-(3-fluoro-phenyl)-pyrrolidine

The title compound, white solid, m.p. 126° C. and MS: m/e=339 (M$^+$) was prepared in accordance with the general method of example 1e from (RS)-2-(3-fluoro-phenyl)-pyrrolidine and 4-chloro-benzenesulfonyl chloride.

EXAMPLE 3

(RS)-4-[1-(Toluene-4-sulfonyl)-pyrrolidin-2-yl]-pyridine

The title compound, pale brown solid, m.p. 158° C. and MS: m/e=302 (M$^+$) was prepared in accordance with the general method of example 1e from (RS)-4-(2-pyrrolidinyl)-pyridine and toluene-4-sulfonyl chloride.

EXAMPLE 4

(RS)-2-Phenyl-1-(toluene-4-sulfonyl)-pyrrolidine

The title compound, white solid, m.p. 109° C. and MS: m/e=301 (M$^+$) was prepared in accordance with the general method of example 1e from (RS)-2-phenyl-pyrrolidine and toluene-4-sulfonyl chloride.

EXAMPLE 5

(RS)-1-Benzenesulfonyl-2- phenyl-pyrrolidine

The title compound, light pink solid, m.p. 116° C. and MS: m/e=287 (M$^+$) was prepared in accordance with the general method of example 1e from (RS)-2-phenyl-pyrrolidine and benzenesulfonyl chloride.

EXAMPLE 6

(RS)-1-(4-Chloro-benzenesulfonyl)-2-phenyl-pyrrolidine

The title compound, pale pink solid, m.p. 119° C. and MS: m/e=321 (M$^+$) was prepared in accordance with the general method of example 1e from (RS)-2-phenyl-pyrrolidine and 4-chloro-benzenesulfonyl chloride.

EXAMPLE 7

(RS)-1- Benzenesulfonyl-2-(4-fluoro-phenyl)-pyrrolidine

The title compound, white solid, m.p. 100° C. and MS: m/e=305 (M$^+$) was prepared in accordance with the general method of example 1e from (RS)-2-(4-fluoro-phenyl)-pyrrolidine and benzenesulfonyl chloride.

EXAMPLE 8

(RS)-2-(4-Chloro-phenyl)-1-(toluene-4-sulfonyl)-pyrrolidine

The title compound, white solid, m.p. 121° C. and MS: m/e=335 (M$^+$) was prepared in accordance with the general method of example 1e from (RS)-2-(4-chloro-phenyl)-pyrrolidine and toluene-4-sulfonyl chloride.

EXAMPLE 9

(RS)-1-(4-Chloro-benzenesulfonyl)-2-(4-chloro-phenyl)-pyrrolidine

The title compound, white solid, m.p. 159° C. and MS: m/e=355 (M$^+$) was prepared in accordance with the general method of example 1e from (RS)-2-(4-chloro-phenyl)-pyrrolidine and 4-chloro-benzenesulfonyl chloride.

EXAMPLE 10

(RS)-2-(4-Fluoro-phenyl)-1-(4-methoxy-benzenesulfonyl)-pyrrolidine

The title compound, white solid, m.p. 134° C. and MS: m/e=335 (M$^+$) was prepared in accordance with the general method of example I e from (RS)-2-(4-fluoro-phenyl)-pyrrolidine and 4-methoxy-benzenesulfonyl chloride.

EXAMPLE 11

(RS)-1-(4-Chloro-benzenesulfonyl)-2-(4-fluorophenyl)-pyrrolidine

The title compound, white solid, m.p. 118° C. and MS: m/e=339 (M$^+$) was prepared in accordance with the general method of example 1e from (RS)-2-(4-fluoro-phenyl)-pyrrolidine and 4-chloro-benzenesulfonyl chloride.

EXAMPLE 12

(RS)-2-(4-Fluoro-phenyl)-1-(toluene-4-sulfonyl)-pyrrolidine

The title compound, off-white solid, m.p. 128° C. and MS: m/e=319 (M$^+$) was prepared in accordance with the general method of example 1e from (RS)-2-(4-fluoro-phenyl)-pyrrolidine and toluene-4-sulfonyl chloride.

EXAMPLE 13

(RS)-1-Benzenesulfonyl-2-(4-chloro-phenyl)-pyrrolidine

The title compound, white solid, m.p. 122° C. and MS: m/e=321 (M$^+$) was prepared in accordance with the general method of example 1e from (RS)-2-(4-chloro-phenyl)-pyrrolidine and benzenesulfonyl chloride.

EXAMPLE 14

(RS)-4-1-(4-Chloro-benzenesulfonyl)-pyrrolidine-pyridine

The title compound, white solid, m.p. 177° C. and MS: m/e=322 (M$^+$) was prepared in accordance with the general method of example 1e from (RS)-4-(pyrrolidin-2-yl)-pyridine and 4-chloro-benzenesulfonyl chloride.

EXAMPLE 15

(RS)-1-Benzenesulfonyl-2-(3-fluoro-phenyl)-pyrrolidine

The title compound, white solid, m.p. 96° C. and MS: m/e=305 (M$^+$) was prepared in accordance with the general method of example 1e from (RS)-2-(3-fluoro-phenyl)-pyrrolidine and benzenesulfonyl chloride.

EXAMPLE 16

(RS)-1-(4-Fluoro-benzenesulfonyl)-2-(4-fluoro-phenyl)-pyrrolidine

The title compound, light brown solid, m.p. 121° C. and MS: m/e=324.2 (M+H$^+$) was prepared in accordance with the general method of example 1e from (RS)-2-(4-fluoro-phenyl)-pyrrolidine and 4-fluoro-benzenesulfonyl chloride.

EXAMPLE 17

(RS)-2-(4-Fluoro-phenyl)-1-(toluene-3-sulfonyl)-pyrrolidine

The title compound, light brown solid, m.p. 102° C. and MS: m/e=319 (M$^+$) was prepared in accordance with the general method of example 1e from (RS)-2-(4-fluoro-phenyl)-pyrrolidine and toluene-3-sulfonyl chloride.

EXAMPLE 18

(RS)-2-(4-Fluoro-phenyl)-1-(toluene-2-sulfonyl)-pyrrolidine

The title compound, colorless oil, MS: m/e=319 (M$^+$) was prepared in accordance with the general method of example 1e from (RS)-2-(4-fluoro-phenyl)-pyrrolidine and toluene-2-sulfonyl chloride.

EXAMPLE 19

(RS)-1-(Toluene-4-sulfonyl)-2-p-tolyl-pyrrolidine

The title compound, white solid, m.p. 124° C. and MS: m/e=315 (M$^+$) was prepared in accordance with the general method of example 1e from (RS)-2-p-tolyl-pyrrolidine and toluene-4-sulfonyl chloride.

EXAMPLE 20

(RS)-1-(4-Chloro-benzenesulfonyl)-2-p-tolyl-pyrrolidine

The title compound, white solid, m.p. 129° C. and MS: m/e=335 (M$^+$) was prepared in accordance with the general method of example 1e from (RS)-2-p-tolyl-pyrrolidine and 4-chloro-benzenesulfonyl chloride.

EXAMPLE 21

(RS)-1-(4-Ethyl-benzenesulfonyl)-2-(4-fluoro-Rhenyl)-pyrrolidine

The title compound, white solid, m.p. 78° C. and MS: m/e=333 (M$^+$) was prepared in accordance with the general method of example 1e from (RS)-2-(4-fluoro-phenyl)-pyrrolidine and 4-ethyl-benzenesulfonyl chloride.

EXAMPLE 22

(RS)-2-(4-Fluoro-phenyl)-1-(4-isopropyl-benzenesulfonyl)-pyrrolidine

The title compound, white solid, m.p. 77° C. and MS: m/e=347 (M$^+$) was prepared in accordance with the general method of example 1e from (RS)-2-(4-fluoro-phenyl)-pyrrolidine and 4-isopropyl-benzenesulfonyl chloride.

EXAMPLE 23

(RS)-1-(4-Fluoro-benzenesulfonyl)-2-p-tolyl-pyrrolidine

The title compound, white solid, m.p. 112° C. and MS: m/e=319 (M$^+$) was prepared in accordance with the general method of example 1e from (RS)-2-p-tolyl-pyrrolidine and 4-fluoro-benzenesulfonyl chloride.

EXAMPLE 24

(RS)-1-(4-Chloro-benzenesulfonyl)-2-(4-methoxyl-phenyl)-pyrrolidine

The title compound, white solid, m.p. 133° C. and MS: m/e=352 (M+H$^+$) was prepared in accordance with the general method of example 1e from (RS)-2-(4-methoxy-phenyl)-pyrrolidine and 4-chloro-benzenesulfonyl chloride.

EXAMPLE 25

(RS)-2-(4-Methoxy-phenyl)-1-(toluene-4-sulfonyl)-pyrrolidine

The title compound, white solid, m.p. 122° C. and MS: m/e=332 (M+H$^+$) was prepared in accordance with the general method of example 1e from (RS)-2-(4-methoxy-phenyl)-pyrrolidine and toluene-4-sulfonyl chloride.

EXAMPLE 26

(RS)-1-(4-Bromo-benzenesulfonyl)-2-(4-fluoro-phenyl)-pyrrolidine

The title compound, off-white solid, m.p. 131° C. and MS: m/e=383 (M$^+$) was prepared in accordance with the general method of example 1e from (RS)-2-(4-fluoro-phenyl)-pyrrolidine and 4-bromo-benzenesulfonyl chloride.

EXAMPLE 27

(RS)-1-{4-[2-(4-Fluoro-phenyl)-pyrrolidine-1-sulfonyl]-phenyl}-ethanone

The title compound, pale brown solid, m.p. 148° C. and MS: m/e=348 (M+H$^+$) was prepared in accordance with the general method of example 1e from (RS)-2-(4-fluoro-phenyl)-pyrrolidine and 4-acetyl-benzenesulfonyl chloride.

EXAMPLE 28

(RS)-1-(Toluene-4-sulfonyl)-2-m-tolyl-pyrrolidine

The title compound, off-white solid, m.p. 79° C. and MS: m/e=315 (M$^+$) was prepared in accordance with the general method of example 1e from (RS)-2-m-tolyl-pyrrolidine and toluene-4-sulfonyl chloride.

EXAMPLE 29

(RS)-1-(4-Chloro-benzenesulfonyl)-2-m-tolyl-pyrrolidine

The title compound, off-white solid, m.p. 78° C. and MS: m/e=335 (M$^+$) was prepared in accordance with the general method of example 1e from (RS)-2-m-tolyl-p yrrolidine and 4-cho-benzenesulfonyl chloride.

EXAMPLE 30

(RS)-1-(4-Fluoro-benzenesulfonyl)-2-m-tolyl-pyrrolidine

The title compound, off-white solid, m.p. 80° C. and MS: m/e=319(M$^+$) was prepared in accordance with the general method of example 1e from (RS)-2-m-tolyl-pyrrolidine and 4-fluoro-benzenesulfonyl chloride.

EXAMPLE 31

(RS)-2-(3-Chloro-phenyl)-1-(toluene -4-sulfonyl)-pyrrolidine

The title compound, off-white solid, m.p. 107° C. and MS: m/e=335 (M$^+$) was prepared in accordance with the general method of example 1e from (RS)-2-(3-chloro-phenyl)-pyrrolidine and toluene-4-sulfonyl chloride.

EXAMPLE 32

(RS)-1-(4-Chloro-benzenesulfonyl)-2-(3-chloro-phenyl)-pyrrolidine

The title compound, light brown solid, m.p. 99° C. and MS: m/e=355 (M$^+$) was prepared in accordance with the general method of example 1e from (RS)-2-(3-chloro-phenyl)-pyrrolidine and 4-chloro-benzenesulfonyl chloride.

EXAMPLE 33

(RS)-2-(4-Fluoro-phenyl)-1-(4-cyano-benzenesulfonyl)-pyrrolidine

The title compound, off-white solid, m.p. 147° C. and MS: m/e=330 (M$^+$) was prepared in accordance with the general method of example 1e from (RS)-2-(4-fluoro-phenyl)-pyrrolidine and 4-cyano-benzenesulfonyl chloride.

EXAMPLE 34

(RS)-1-(4-Chloro-benzenesulfonyl)-2-(3-methoxy-phenyl)-pyrrolidine

The title compound, white solid, m.p. 95° C. and MS: m/e=351 (M$^+$) was prepared in accordance with the general method of example 1e from (RS)-2-(3-methoxy-phenyl)-pyrrolidine and 4-chloro-benzenesulfonyl chloride.

EXAMPLE 35

(RS)-1-(4-Fluoro-benzenesulfonyl)-2-thien-2-yl-pyrrolidine

The title compound, white solid, m.p. 97° C. and MS: m/e=312.1 (M+H$^+$) was prepared in accordance with the general method of example 1e from (RS)-2-thien-2-yl-pyrrolidine and 4-fluoro-benzenesulfonyl chloride.

EXAMPLE 36

(RS)-1-(4-Chloro-benzenesulfonyl)-2-thien-2-yl-pyrrolidine

The title compound, white solid, m.p. 84° C. and MS: m/e=328.1 (M+H+) was prepared in accordance with the general method of example 1e from (RS)-2-thien-2-yl-pyrrolidine and 4-chloro-benzenesulfonyl chloride.

EXAMPLE 37

(RS)-2-Thien-2-yl-1-(toluene-4-sulfonyl)-pyrrolidine

The title compound, white solid, m.p. 108° C. and MS: m/e=308.2 (M+H$^+$) was prepared in accordance with the general method of example 1e from (RS)-2-thien-2-yl-pyrrolidine and toluene-4-sulfonyl chloride.

EXAMPLE 38

(RS)-2-(3,4-Difluoro-phenyl)-1-(toluene-4-sulfonyl)-pyrrolidine

The title compound, white solid, m.p. 127° C. and MS: m/e=338.2 (M+H$^+$) was prepared in accordance with the general method of example 1e from (RS)-2-(3,4-difluoro-phenyl)-pyrrolidine and toluene-4-sulfonyl chloride.

EXAMPLE 39

(RS)-1-(4-Chloro-benzenesulfonyl)-2-(3,4-difluoro-phenyl)-pyrrolidine

The title compound, white solid, m.p. 121° C. and MS: m/e=358.1 (M+H$^+$) was prepared in accordance with the general method of example 1e from (RS)-2-(3,4-difluoro-phenyl)-pyrrolidine and 4-chloro-benzenesulfonyl chloride.

EXAMPLE 40

(RS)-1-(4-Chloro-benzenesulfonyl)-2-(4-dimethylamino-3-fluoro-phenyl)-pyrrolidine The title compound, white solid, m.p. 99° C. and MS: m/e=383.2 (M+H$^+$) was prepared in accordance with the general method of example 1e from (RS)-2-(4-dimethylamino-3-fluoro-phenyl)-pyrrolidine and 4-chloro-benzenesulfonyl chloride.

EXAMPLE 41

(RS)-1-(p-Toluenesulfonyl)-2-(4-dimethylamino-3-fluoro-phenyl)-pyrrolidine

The title compound, white solid, m.p. 66° C. and MS: m/e=363.1 (M+H$^+$) was prepared in accordance with the general method of example 1e from (RS)-2-(4-dimethylamino-3-fluoro-phenyl)-pyrrolidine toluene-4-sulfonyl chloride.

EXAMPLE 42

(RS)-2-(3-Chloro-4-fluoro-phenyl)-1-(toluene-4-sulfonyl)-pyrrolidine

The title compound, off-white solid, m.p. 96° C. and MS: m/e=354.2 (M+H$^+$) was prepared in accordance with the general method of example 1e from (RS)-2-(3-chloro-4-fluoro-phenyl)-pyrrolidine and toluene-4-sulfonyl chloride.

EXAMPLE 43

(RS)-1-(4-Chloro-benzenesulfonyl)-2-(3-chloro-4-fluoro-phenyl)-pyrrolidine

The title compound, off-white solid, m.p. 119° C. and MS: m/e=374.2 (M+H$^+$) was prepared in accordance with the general method of example 1e from (RS)-2-(3-chloro-4-fluoro-phenyl)-pyrrolidine and 4-chloro-benzenesulfonyl chloride.

EXAMPLE 44

(RS)-2-(3-Chloro-4-fluoro-phenyl)-1-(4-fluoro-benzenesulfonyl)-pyrrolidine

The title compound, white solid, m.p. 116° C. and MS: m/e=358.1 (M$^+$) was prepared in accordance with the general method of example 1e from (RS)-2-(3-chloro-4-fluoro-phenyl)-pyrrolidine and 4-fluoro-benzenesulfonyl chloride.

EXAMPLE 45

(RS)-1-(4-Chloro-benzenesulfonyl)-2-(4-dimethylamino-3-chloro-phenyl)-pyrrolidine The title compound, white solid, m.p. 103° C. and MS: m/e=398 (M$^+$) was prepared in accordance with the general method of example 1e from (RS)-2-(4-dimethylamino-3-chloro-phenyl)-pyrrolidine and 4-chloro-benzenesulfonyl chloride.

EXAMPLE 46

(RS)-1-(4-fluoro-benzenesulfonyl)-2-(4-diimethylamino-3-chloro-phenyl)-pyrrolidine The title compound, off-white solid, m.p. 119° C. and MS: m/e=382 (M$^+$) was prepared in accordance with the general method of example 1e from (RS)-2-(4-dimethylamino-3-chloro-phenyl)-pyrrolidine and 4-fluoro-benzenesulfonyl chloride.

EXAMPLE 47

(RS)-2-(3,4-Dichloro-phenyl )-1-(toluene-4-sufonyl)- pyrrolidine

The title compound, off-white solid, m.p. 136° C. and MS: m/e=369 (M$^+$) was prepared in accordance with the general method of example 1e from (RS)-2-(3,4-dichloro-phenyl)-pyrrolidine and tolutene-4-sulfonyl chloride.

EXAMPLE 48

(RS)-1-(Toluene-4-sulfonyl)-2-(4-trifluoromethyl-phenyl)-pyrrolidine

The title compound, white solid, m.p. 99° C. and MS: m/e=369 (M$^+$) was prepared in accordance with the general method of example 1e from (RS)-2-(4-trifluoromethyl-phenyl)-pyrrolidine and toluene-4-sulfonyl chloride.

EXAMPLE 49

(RS)-1-(4Chloro-benzenesulfonyl)-2-(4-trifluoromethyl-phenyl)-pyrrolidine

The title compound, white solid, m.p. 107° C. and MS: m/e=369 (M$^+$) was prepared in accordance with the general method of example 1e from (RS)-2-(4-trifluoromethyl-phenyl)-pyrrolidine and 4-chloro-benzenesulfonyl chloride.

EXAMPLE 50

(RS)-1-(4-Floro-benzenesulfonyl)-2-(4-trifluoromethyl-phenyl)-pyrrolidine

The title compound, white solid, m.p. 114° C. and MS: m/e=373 (M$^+$) was prepared in accordance with the general method of example 1e from (RS)-2-(4-trifluoromethyl-phenyl)-pyrrolidine and 4-fluoro-benzenesulfonyl chloride.

EXAMPLE 51

(RS)-2-(2-Chloro-phenyl)-1-(toluene-4-sulfonyl)-pyrrolidine

The title compound, white solid, m.p. 149° C. and MS: m/e=336.2 (M+H$^+$) was prepared in accordance with the general method of example 1e from (RS)-2-(2-chloro-phenyl)-pyrrolidine and toluene-4-sulfonyl chloride.

EXAMPLE 52

(RS)-2-(2-Fluoro-phenyl)-1-(toluene-4-sulfonyl)-pyrrolidine

The title compound, white solid, m.p. 143° C. and MS: m/e=320.3 (M+H$^+$) was prepared in accordance with the general method of example 1e from (RS)-2-(2-fluoro-phenyl)-pyrrolidine and toluene-4-sulfonyl chloride.

EXAMPLE 53

(RS)-1-(4-Chloro-benzenesulfonyl)-2-(2-fluoro-phenyl)-pyrrolidine

The title compound, white solid, m.p. 134° C. and MS: m/e=340.2 (M+H$^+$) was prepared in accordance with the general method of example 1e from (RS)-2-(2-fluoro-phenyl)-pyrrolidine and 4-chloro-benzenesulfonyl chloride.

EXAMPLE 54

(RS)-1-(4-Fluoro-benzenesulfonyl)-2-(2-fluoro-phenyl)-pyrrolidine

The title compound, white solid, m.p. 108° C. and MS: m/e=324.2 (M+H$^+$) was prepared in accordance with the general method of example 1e from (RS)-2-(2-fluoro-phenyl)-pyrrolidine and 4-fluoro-benzenesulfonyl chloride.

EXAMPLE 55

(RS)-2-Thien-3-yl-1-(toluene-4-sulfonyl)-pyrrolidine

The title compound, white solid, m.p. 114° C. and MS: m/e=308.2 (M+H$^+$) was prepared in accordance with the general method of example 1e from (RS)-2-thien-3-yl-pyrrolidine and toluene-4-sulfonyl chloride.

EXAMPLE 56

(RS)-1-(4-Chloro-benzenesulfonyl)-2-thien-3-yl-pyrrolidine

The title compound, white solid, m.p. 120° C. and MS: m/e=328.1 (M+H$^+$) was prepared in accordance with the general method of example 1e from (RS)-2-thien-3-yl-pyrrolidine and 4-chloro-benzenesulfonyl chloride.

EXAMPLE 57

(RS)-1-(4-Fluoro-benzenesulfonyl)-2-thien-3-yl-pyrrolidine

The title compound, white solid, m.p. 135° C. and MS: m/e=312.1 (M+H$^+$) was prepared in accordance with the general method of example 1e from (RS)-2-thien-3-yl-pyrrolidine and 4-fluoro-benzenesulfonyl chloride.

EXAMPLE 58

(RS)-2-(4-Chloro-3-methyl-phenyl)-1-(toluene-4-sulfonyl)-pyrrolidine

The title compound, white solid, m.p. 103° C. and MS: m/e=349 (M$^+$) was prepared in accordance with the general method of example 1e from (RS)-2-(4-chloro-3-methyl-phenyl)-pyrrolidine and toluene-4-sulfonyl chloride.

EXAMPLE 59

(RS)-2-(4-Fluoro-phenyl)-1-(4-propyl-benzenesulfonyl)-pyrrolidine

The title compound, colorless oil, MS: m/e=347 (M$^+$) was prepared in accordance with the general method of example 1e from (RS)-2-(4-fluoro-phenyl)-pyrrolidine and 4-propyl-benzenesulfonyl chloride.

EXAMPLE 60

(RS)-2-(4-Fluoro-phenyl)-1-(4-trifluoromethyl-benzenesulfonyl)-pyrrolidine

The title compound, white solid, m.p. 85° C. and MS: m/e=373 (M$^+$) was prepared in accordance with the general method of example 1e from (RS)-2-(4-fluoro-phenyl)-pyrrolidine and 4-trifluoromethyl-benzenesulfonyl chloride.

EXAMPLE 61

(RS)-2-(4-Fluoro-phenyl)-1-(2,4,6-trimethyl-benzenesulfonyl)-pyrrolidine

The title compound, white solid, m.p. 111° C. and MS: m/e=347 (M$^+$) was prepared in accordance with the general method of example 1e from (RS)-2-(4-fluoro-phenyl)-pyrrolidine and 2,4,6-trimethyl-benzenesulfonyl chloride.

EXAMPLE 62

(RS)-1-(3-Chloro-4-methyl-benzenesulfonyl)-2-(4-fluoro-phenyl)-pyrrolidine

The title compound, off-white solid, m.p. 134° C. and MS: m/e=353 (M$^+$) was prepared in accordance with the general method of example 1e from (RS)-2-(4-fluoro-phenyl)-pyrrolidine and 3-chloro-4-methyl-benzenesulfonyl chloride.

EXAMPLE 63

(RS)-1-(2-Fluoro-benzenesulfonyl)-2-(4-fluoro-phenyl)-pyrrolidine

The title compound, off-white solid, m.p.91° C. and MS: m/e=323 (M$^+$) was prepared in accordance with the general method of example 1e from (RS)-2-(4-fluoro-phenyl)-pyrrolidine and 2-fluoro-benzenesulfonyl chloride.

EXAMPLE 64

(RS)-1-(3-Fluoro-benzenesulfonyl)-2-(4-fluoro-phenyl)-pyrrolidine

The title compound, off-white solid, m.p. 101° C. and MS: m/e=323 (M$^+$) was prepared in accordance with the general method of example 1e from (RS)-2-(4-fluoro-phenyl)-pyrrolidine and 3-fluoro-benzenesulfonyl chloride.

EXAMPLE 65

(RS)-1-(2-Cyano-benzenesulfonyl)-2-(4-fluoro-phenyl)-pyrrolidine

The title compound, light green solid, m.p. 101° C. and MS: m/e=330 (M$^+$) was prepared in accordance with the general method of example 1e from (RS)-2-(4-fluoro-phenyl)-pyrrolidine and 2-cyano-benzenesulfonyl chloride.

EXAMPLE 66

(RS)-2-(4-Fluoro-phenyl)-1-(naphthalene-2-sulfonyl)-pyrrolidine

The title compound, off-white solid, m.p. 166° C. and MS: m/e=355 (M$^+$) was prepared in accordance with the general method of example 1e from (RS)-2-(4-fluoro-phenyl)-pyrrolidine and naphthalene-2-sulfonyl chloride.

EXAMPLE 67

(RS)-2-(2,4-Dimethyl-phenyl)-1-(toluene-4-sulfonyl)-pyrrolidine

The title compound, white solid, m.p. 130° C. and MS: m/e=329 (M$^+$) was prepared in accordance with the general method of example 1e from (RS)-2-(2,4-dimethyl-phenyl)-pyrrolidine and toluene-4-sulfonyl chloride.

EXAMPLE 68

(RS)-2-(2,4-Dimethyl-phenyl)-1-(4-fluoro-benzenesulfonyl)-pyrrolidine

The title compound, white solid, m.p. 134° C. and MS: m/e=333 (M$^+$) was prepared in accordance with the general method of example 1e from (RS)-2-(2,4-dimethyl-phenyl)-pyrrolidine and 4-fluoro-benzenesulfonyl chloride.

EXAMPLE 69

(RS)-2-Furan-2-yl-1-(toluene-4-sulfonyl)-pyrrolidine

The title compound, white solid, m.p. 58° C. and MS: m/e=291 (M$^+$) was prepared in accordance with the general method of example 1e from (RS)-2-furan-2-yl-pyrrolidine and toluene-4-sulfonyl chloride.

EXAMPLE 70

(RS)-1-(4-Fluoro-benzenesulfonyl)-2-furan-2-yl-pyrrolidine

The title compound, white solid, m.p. 69° C. and MS: m/e=295 (M$^+$) was prepared in accordance with the general method of example 1e from (RS)-2-furan-2-yl-pyrrolidine and 4-fluoro-benzenesulfonyl chloride.

EXAMPLE 71

(RS)-1-(4-Chloro-benzenesulfonyl)-2-furan-2-yl-pyrrolidine

The title compound, yellow oil, MS: m/e=311 (M$^+$) was prepared in accordance with the general method of example 1e from (RS)-2-furan-2-yl-pyrrolidine and 4-chloro-benzenesulfonyl chloride.

EXAMPLE 72

(RS)-2-(4-N,N-Dimethylamino-phenyl)-1-(toluene-4-sulfonyl)-pyrrolidine

The title compound, white solid, m.p. 132° C. and MS: m/e=345.3 (M+H$^+$) was prepared in accordance with the general method of example 1e from (RS)-2-(4-N,N-dimethylamino-phenyl)-pyrrolidine and toluene-4-sulfonyl chloride.

EXAMPLE 73

(RS)-2-(4-N,N-Dimethylamino-phenyl)-1-(4-fluoro-benzenesulfonyl)-pyrrolidine

The title compound, white solid, m.p. 109° C. and MS: m/e=349.4 (M+H$^+$) was prepared in accordance with the general method of example 1e from (RS)-2-(4-N,N-dimethylamino-phenyl)-pyrrolidine and 4-fluoro-benzenesulfonyl chloride.

EXAMPLE 74

(RS)-2-(4-N,N-Dimethylamino-phenyl)-1-(4-chloro-benzenesulfonyl)-pyrrolidine

The title compound, white solid, m.p. 117° C. and MS: m/e=365.2 (M+H$^+$) was prepared in accordance with the general method of example 1e from (RS)-2-(4-N,N-dimethylamino-phenyl)-pyrrolidine and 4-chloro-benzenesulfonyl chloride.

EXAMPLE 75

(RS)-1-Benzenesulfonyl-2-(4-trifluoromethyl-phenyl)-pyrrolidine

The title compound, white solid, m.p. 95° C. and MS: m/e=355 (M$^+$) was prepared in accordance with the general method of example 1e from (RS)-2-(4-trifluoromethyl-phenyl)-pyrrolidine and benzenesulfonyl chloride.

EXAMPLE 76

(R)-1-(4-Chloro-benzenesulfonyl)-2-(4-fluoro-phenyl)-pyrrolidine

The title compound, white solid, m.p. 119° C. and MS: m/e=339 (M$^+$) was prepared in accordance with the general method of example 1e from (R)-2-(4-fluoro-phenyl)-pyrrolidine and 4-chloro-benzenesulfonyl chloride.

EXAMPLE 77

(S)-1-(4-Chloro-benzenesulfonyl)-2-(4-fluoro-phenyl)-pyrrolidine

The title compound, white solid, m.p. 120° C. and MS: m/e=339 (Me) was prepared in accordance with the general method of example 1e from (S)-2-(4-fluoro-phenyl)-pyrrolidine and 4-chloro-benzenesulfonyl chloride.

EXAMPLE 78

(RS)-2-(4-Ethyl-phenyl)-1-(toluene-4-sulfonyl)-pyrrolidine

The title compound, white solid, m.p. 92° C. and MS: m/e=330.3 (M+H$^+$) was prepared in accordance with the general method of example 1e from (RS)-2-(4-ethyl-phenyl)-pyrrolidine and toluene-4-sulfonyl chloride.

EXAMPLE 79

(RS)-2-(4-Ethyl-phenyl)-1-(4-chloro-benzenesulfonyl)-pyrrolidine

The title compound, white solid, m.p. 94° C. and MS: m/e=350.3 (M$^+$) was prepared in accordance with the general method of example 1e from (S)-2-(4-ethyl-phenyl)-pyrrolidine and 4-chloro-benzenesulfonyl chloride.

EXAMPLE 80

(RS)-2-(4-Ethyl-phenyl)-1-(4-fluoro-benzenesulfonyl)-pyrrolidine

The title compound, white solid, m.p. 93° C. and MS: m/e=334.2 (M+H$^+$) was prepared in accordance with the general method of example 1e from (S)-2-(4-ethyl-phenyl)-pyrrolidine and 4-fluoro-benzenesulfonyl chloride.

EXAMPLE 81

(R)-2-(4-Fluoro-phenyl)-1-(toluene-4-sulfonyl)-pyrrolidine

The title compound, white solid, m.p. 136° C., $[a]_D^{20}$=174° (c=0.1 in CHCl$_3$) and MS: m/e=319 (M$^+$) was prepared in accordance with the general method of example 1e from (R)-2-(4-fluoro-phenyl)-pyrrolidine and toluene-4-sulfonyl chloride.

EXAMPLE 82

(S)-2-(4-Fluoro-phenyl)-1-(toluene-4-sulfonyl)-pyrrolidine

The title compound, white solid, m.p. 136° C., $[a]_D^{20}$=172° (c=0.1 in CHCl$_3$) and MS: m/e=319 (M$^+$) was prepared in accordance with the general method of example 1e from (S)-2-(4-fluoro-phenyl)-pyrrolidine and toluene-4-sulfonyl chloride.

EXAMPLE 83

(RS)-3-[1-(Toluene-4-sulfonyl)-pyrrolidin-2-yl]-pyridine

The title compound, white solid, m.p. 112° C., and MS: m/e=302 (M$^+$) was prepared in accordance with the general method of example 1e from 3-(pyrolidin-2-yl)-pyridine and toluene-4-sulfonyl chloride.

EXAMPLE 84

(RS)-2-(4-Fluoro-phenyl)-1-(4-hydroxymethyl-benzenesulfonyl)-pyrrolidine

The title compound, white solid, m.p. 107° C., and MS: m/e=336.2 (M+H$^+$) was prepared in accordance with the general method of example 1e from (RS)-2-(4-fluoro-phenyl)-pyrrolidine and 4-hydroxymethyl-benzenesulfonyl chloride.

EXAMPLE 85

(RS)-2-(4-Fluoro-phenyl)-1-(4-methoxymethyl-benzenesulfonyl)-pyrrolidine

Reaction of (RS)-2-(4-fluoro-phenyl)-1-(4-chloromethyl-benzenesulfonyl)-pyrrolidine (0.50 g, 1.41 mmol), which was prepared in accordance with the general method of example 1e from (RS)-2-(4-fluoro-phenyl)-pyrrolidine and 4-bromomethyl-benzenesulfonyl chloride, with sodium methanolate in MeOH for 80 h at 50° C. yielded after crystallization from EE/hexane 0.28 g (52%) of the title compound as a white solid, m.p. 115° C., and MS: m/e=349 (M$^+$).

EXAMPLE 86

(RS)-4-{4-[2-(4-Fluoro-phenyl)-pyrrolidine-1-sulfonyl]-benzyl}-morpholine fumarate (1:1)

Reaction of (RS)-2-(4-fluoro-phenyl)-1-(4-chloromethyl-benzenesulfonyl)-pyrrolidine (0.50 g, 1.41 mmol), which was prepared in accordance with the general method of example 1e from (RS)-2-(4-fluoro-phenyl)-pyrrolidine and 4-bromomethyl-benzenesulfonyl chloride, with morpholine (K$_2$CO$_3$, DMF, 80° C., 17 h) and subsequent formation of the fumarate (MeOH, diethyl ether) yielded the title compound as an off-white solid, m.p. 136° C., and MS: m/e= 405.4 (M+H$^+$).

EXAMPLE 87

(RS)-4-[2-(4-Fluoro-phenyl)-pyrrolidine-1-sulfonyl]-benzylamine fumarate (1:0.5)

Hydrogenation of (RS)-2-(4-fluoro-phenyl)-1-(4-cyano-benzenesulfonyl)-pyrrolidine (Ra-Ni, MeOH-NH$_3$) and subsequent formation of the fumarate (MEOH, diethyl ether) yielded the title compound as a white solid, m.p. 207° C., and MS: m/e=335.2 (M+H$^+$).

EXAMPLE 88

Mixture of (2RS,3RS )- and (2RS,3SR)-2-(4-fluoro-phenyl)-3-methyl-1-(toluene-1-sufonyl)-pyrrolidine The title compound, off-white solid, m.p. 94° C. and MS: me=3 (M$^+$) was prepared in accordance with the general method of example 1e from a mixture of (2RS,3 RS)- and (2RS,3 SR)-2-(4-fluorophenyl)-3-methyl-pyrrolidine and toluene-4-sulfonyl chloride.

EXAMPLE 89

Mixture of (2RS,3RS)- and (2RS,3 SR)-1-(4-chloro-benzenesulfonyl)-2-(4-fluoro-phenyl)-3-methyl-pyrrolidine The title compound, off-white solid, m.p. 87° C. and MS: m/e=354.2 (M+H$^+$) was prepared in accordance with the general method of example 1e from a mixture of (2RS,3RS)- and (2RS,3SR)-2-(4-fluoro-phenyl)-3-methyl-pyrrolidine and 4-chlorobenzene-sulfonyl chloride.

EXAMPLE 90

(2RS,3RS)-2-(4-Fluoro-phenyl)-3-methyl-1-(toluene-4-sulfonyl)-pyrrolidine

The title compound, off-white solid, m.p. 112° C. and MS: m/e=354.2 (M$^+$) was prepared in accordance with the general method of example 1e from (2RS,3RS)-2-(4-fluoro-phenyl)-3-methyl-pyrrolidine and toluene-4-sulfonyl chloride.

EXAMPLE 91

(2RS,3 RS)-[2-(4-Fluoro-phenyl)-1-(toluene-4-sulfonyl)-pyrrolidin-3-yl]-methanol Reduction of (2RS,3RS)-2-(4-fluoro-phenyl)-1-(toluene-4-sulfonyl)-pyrrolidine-3-carboxylic acid methyl ester, prepared from (2RS,3RS)-2-(4-fluoro-phenyl)-pyrrolidine-3-carboxylic acid methyl ester and toluene-4-sulfonyl chloride in accordance with the general method of example 1e, with sodium boron hydride in MeOH yielded after aqueous work-up and purification by column chromatography on silica gel (ethyl acetate/hexane 1:1) the title compound as a pale yellow oil, MS: m/e=348 (M−H$^+$).

Table 1 sets for the the subtituents for each compound of the previously described Examples

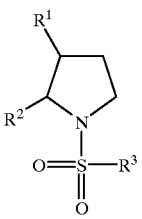

| Example | R$^1$ | R$^2$ | R$^3$ | Remarks |
|---|---|---|---|---|
| 1 | H | 3-F-phenyl | 4-methyl-phenyl | Agonist |
| 2 | H | 3-F-phenyl | 4-Cl-phenyl | Agonist |
| 3 | H | 4-pyridyl | 4-methyl-phenyl | Agonist |

-continued

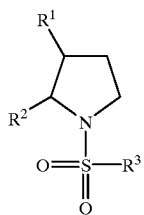

| Example | R¹ | R² | R³ | Remarks |
|---|---|---|---|---|
| 4 | H | phenyl | 4-methylphenyl | Agonist known compound |
| 5 | H | phenyl | phenyl | |
| 6 | H | phenyl | 4-chlorophenyl | Agonist |
| 7 | H | 4-fluorophenyl | phenyl | Antagonist |
| 8 | H | 4-chlorophenyl | 4-methylphenyl | Agonist |
| 9 | H | 4-chlorophenyl | 4-chlorophenyl | Agonist |
| 10 | H | 4-fluorophenyl | 4-methoxyphenyl | Antagonist |
| 11 | H | 4-fluorophenyl | 4-chlorophenyl | Agonist |
| 12 | H | 4-fluorophenyl | 4-methylphenyl | Agonist |
| 13 | H | 4-chlorophenyl | phenyl | Agonist |

-continued

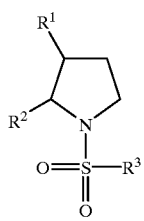

| Example | R¹ | R² | R³ | Remarks |
|---|---|---|---|---|
| 14 | H | 4-pyridyl | 4-Cl-phenyl | Agonist |
| 15 | H | 3-F-phenyl | phenyl | |
| 16 | H | 4-F-phenyl | 4-F-phenyl | Agonist |
| 17 | H | 4-F-phenyl | 3-methylphenyl | |
| 18 | H | 4-F-phenyl | 2,3-dimethylphenyl | Antagonist |
| 19 | H | 4-methylphenyl | 4-methylphenyl | Agonist known compound |
| 20 | H | 4-methylphenyl | 4-Cl-phenyl | Antagonist |
| 21 | H | 4-F-phenyl | 4-ethylphenyl | Agonist |
| 22 | H | 4-F-phenyl | 4-isopropylphenyl | Antagonist |
| 23 | H | 4-methylphenyl | 4-F-phenyl | Antagonist |

-continued

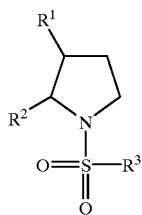

| Example | R¹ | R² | R³ | Remarks |
|---|---|---|---|---|
| 24 | H | -O-C₆H₅-OMe (3-methoxyphenyl) | -C₆H₄-Cl (4-chlorophenyl) | Antagonist |
| 25 | H | 3-methoxyphenyl | 4-methylphenyl | Agonist |
| 26 | H | 4-fluorophenyl | 4-bromophenyl | Agonist |
| 27 | H | 4-fluorophenyl | 4-acetylphenyl | Antagonist |
| 28 | H | 3-methylphenyl | 4-methylphenyl | Agonist |
| 29 | H | 3-methylphenyl | 4-chlorophenyl | Agonist |
| 30 | H | 3-methylphenyl | 4-fluorophenyl | Antagonist |
| 31 | H | 3-chlorophenyl | 4-methylphenyl | Agonist |
| 32 | H | 3-chlorophenyl | 4-chlorophenyl | Antagonist |
| 33 | H | 4-fluorophenyl | 4-cyanophenyl | Antagonist |

-continued

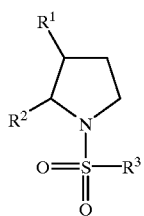

| Example | R¹ | R² | R³ | Remarks |
|---|---|---|---|---|
| 34 | H | 3-methoxyphenyl | 4-Cl-phenyl | Antagonist |
| 35 | H | 2-thienyl | 4-F-phenyl | Antagonist |
| 36 | H | 2-thienyl | 4-Cl-phenyl | Antagonist |
| 37 | H | 2-thienyl | 4-methylphenyl | Antagonist |
| 38 | H | 3,4-difluorophenyl | 4-methylphenyl | Agonist |
| 39 | H | 3,4-difluorophenyl | 4-Cl-phenyl | Agonist |
| 40 | H | 3-fluoro-4-(dimethylamino)phenyl | 4-Cl-phenyl | Agonist |
| 41 | H | 3-fluoro-4-(dimethylamino)phenyl | 4-methylphenyl | Antagonist |
| 42 | H | 3-chloro-4-fluorophenyl | 4-methylphenyl | Agonist |
| 43 | H | 3-chloro-4-fluorophenyl | 4-Cl-phenyl | Antagonist |

-continued
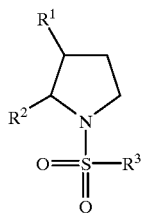
| Example | R¹ | R² | R³ | Remarks |
|---|---|---|---|---|
| 44 | H | 3-Cl, 4-F-phenyl | 4-F-phenyl | Antagonist |
| 45 | H | 2-Cl, 4-(N,N-dimethylamino)-phenyl | 4-Cl-phenyl | Antagonist |
| 46 | H | 2-Cl, 4-(N,N-dimethylamino)-phenyl | 4-F-phenyl | Antagonist |
| 47 | H | 3,4-diCl-phenyl | 4-methyl-phenyl | Antagonist |
| 48 | H | 4-CF₃-phenyl | 4-Cl-phenyl | Agonist |
| 49 | H | 4-CF₃-phenyl | 4-Cl-phenyl | Antagonist |
| 50 | H | 4-CF₃-phenyl | 4-F-phenyl | Antagonist |
| 51 | H | 2-Cl-phenyl | 4-methyl-phenyl | Antagonist |

-continued

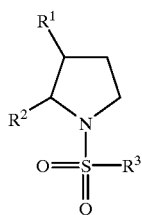

| Example | R¹ | R² | R³ | Remarks |
|---|---|---|---|---|
| 52 | H | 2-fluorophenyl | 4-methylphenyl | |
| 53 | H | 2-fluorophenyl | 4-chlorophenyl | |
| 54 | H | 2-fluorophenyl | 4-fluorophenyl | |
| 55 | H | thiophen-3-yl | 4-methylphenyl | Agonist |
| 56 | H | thiophen-3-yl | 4-chlorophenyl | Agonist |
| 57 | H | thiophen-3-yl | 4-fluorophenyl | |
| 58 | H | 4-chloro-2-methylphenyl | 4-methylphenyl | Agonist |
| 59 | H | 4-fluorophenyl | 4-propylphenyl | Antagonist |
| 60 | H | 4-fluorophenyl | 4-trifluoromethylphenyl | Agonist |

-continued
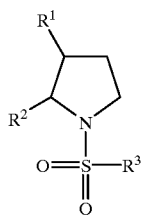
| Example | R¹ | R² | R³ | Remarks |
|---|---|---|---|---|
| 61 | H | 4-F-C₆H₄ | 2,4,6-trimethylphenyl | Antagonist |
| 62 | H | 4-F-C₆H₄ | 2-Cl-4-methylphenyl | Antagonist |
| 63 | H | 4-F-C₆H₄ | 2-F-phenyl | Antagonist |
| 64 | H | 4-F-C₆H₄ | 3-F-phenyl | Antagonist |
| 65 | H | 4-F-C₆H₄ | 2-CN-phenyl | Antagonist |
| 66 | H | 4-F-C₆H₄ | 2-naphthyl | Antagonist |
| 67 | H | 2,4-dimethylphenyl | 4-methylphenyl | Antagonist |
| 68 | H | 2,4-dimethylphenyl | 4-F-phenyl | Antagonist |

-continued

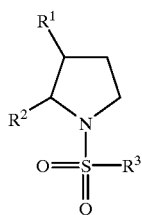

| Example | R¹ | R² | R³ | Remarks |
|---|---|---|---|---|
| 69 | H | 2-furyl | 4-methylphenyl | Agonist |
| 70 | H | 2-furyl | 4-fluorophenyl | Antagonist |
| 71 | H | 2-furyl | 4-chlorophenyl | Antagonist |
| 72 | H | 4-(dimethylamino)phenyl | 4-methylphenyl | Agonist |
| 73 | H | 4-(dimethylamino)phenyl | 4-fluorophenyl | Antagonist |
| 74 | H | 4-(dimethylamino)phenyl | 4-chlorophenyl | Antagonist |
| 75 | H | 4-(trifluoromethyl)phenyl | phenyl | Antagonist |
| 76 | H | 4-fluorophenyl (R) | 4-chlorophenyl | Agonist |
| 77 | H | 4-fluorophenyl (S) | 4-chlorophenyl | Agonist |

-continued

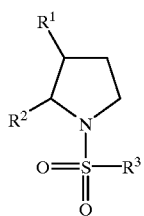

| Example | R¹ | R² | R³ | Remarks |
|---|---|---|---|---|
| 78 | H | 4-ethylphenyl | 4-methylphenyl | Agonist |
| 79 | H | 4-ethylphenyl | 4-chlorophenyl | Antagonist |
| 80 | H | 4-ethylphenyl | 4-fluorophenyl | Antagonist |
| 81 | H | (R)-4-fluorophenyl | 4-methylphenyl | Agonist |
| 82 | H | (S)-4-fluorophenyl | 4-methylphenyl | Agonist |
| 83 | H | pyridin-3-yl | 4-methylphenyl | Agonist |
| 84 | H | 4-fluorophenyl | 4-(methoxymethyl)phenyl | Agonist |
| 85 | H | 4-fluorophenyl | 4-(methoxymethyl)phenyl | Agonist |
| 86 | H | 4-fluorophenyl | 4-(morpholinomethyl)phenyl | Antagonist |
| 87 | H | 4-fluorophenyl | 4-(aminomethyl)phenyl | Antagonist |

-continued

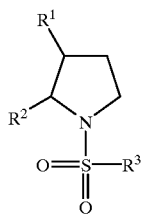

| Example | R¹ | R² | R³ | Remarks |
|---|---|---|---|---|
| 88 | CH₃ | 4-F-C₆H₄ | 4-CH₃-C₆H₄ | agonist |
| 89 | CH₃ | 4-F-C₆H₄ | 4-Cl-C₆H₄ | agonist |
| 90 | CH₃ | 4-F-C₆H₄ | 4-CH₃-C₆H₄ | agonist |
| 91 | CH₂OH | 4-F-C₆H₄ | 4-CH₃-C₆H₄ | agonist |

EXAMPLE A

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compound of formula I:

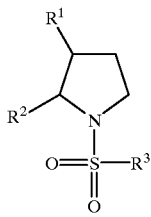

wherein
$R^1$ signifies hydrogen, lower alkyl or hydroxy-lower alkyl;
$R^2$ signifies furyl, thienyl, pyridyl or phenyl, which is optionally substituted by 1 to 3 substituents, selected from lower alkyl, lower alkoxy, halogen, cyano, $CF_3$ or $-N(R^4)_2$;
$R^3$ signifies naphthyl or phenyl, which is optionally substituted by 1 to 3 substituents, selected from lower alkyl, lower alkoxy, halogen, acetyl, cyano, hydroxy-lower alkyl, $-CH_2$-morpholin-4-yl, lower alkyl-oxy-lower alkyl, lower alkyl-$N(R^4)_2$ or $CF_3$;
$R^4$ signifies, independently from each other, hydrogen or lower alkyl,
as well as their pharmaceutically acceptable salts, with the exception of
(RS)-2-phenyl-1-(toluene-4-sulfonyl)-pyrrolidine; and,
(RS)-1-(toluene-4-sulfonyl)-2-p-tolyl-pyrrolidine as well as their pharmaceutically acceptable salts.

2. A compound in accordance with claim 1, wherein
$R^1$ signifies hydrogen or methyl;
$R^2$ signifies phenyl, optionally substituted by halogen, lower alkyl, $CF_3$ or $-N(CH_3)_2$;
and pharmaceutically acceptable salts thereof.

3. A compound according to claim 2, (RS)-2-(3-fluoro-phenyl)-1-(toluene-4-sulfonyl)-pyrrolidine.

4. A compound according to claim 2, (RS)-1-(4-chloro-benzenesulfonyl)-2-(3-fluoro-phenyl)-pyrrolidine.

5. A compound according to claim 2, (RS)-1-(4-chloro-benzenesulfonyl)-2-phenyl-pyrrolidine.

6. A compound according to claim 2, (RS)-1-(4-chloro-phenyl)-1-(toluene-4-sulfonyl)-pyrrolidine.

7. A compound according to claim 2, (RS)-1-(4-chloro-benzenesulfonyl)-2-(4-fluoro-phenyl)-pyrrolidine.

8. A compound according to claim 2, (RS)-2-(4-fluoro-phenyl)-1-(toluene-4-sulfonyl)-pyrrolidine.

9. A compound according to claim 2, (RS)-1-benzenesulfonyl-2-(4-chloro-phenyl)-pyrrolidine.

10. A compound according to claim 2, (RS)-1-(4-fluoro-benzenesulfonyl)-2-(4-fluoro-phenyl)-pyrrolidine.

11. A compound according to claim 2, (RS)-2-(4-fluoro-phenyl)-1-(toluene-2-sulfonyl)-pyrrolidine.

12. A compound according to claim 2, (RS)-1-(4-chloro-benzenesulfonyl)-2-p-tolyl-pyrrolidine.

13. A compound according to claim 2, (RS)-1-(4-ethyl-benzenesulfonyl)-2-(4-fluoro-phenyl)-pyrrolidine.

14. A compound according to claim 2, (RS)-1-(toluene-4-sulfonyl)-2-m-tolyl-pyrrolidine.

15. A compound according to claim 2, (RS)-2-(3-chloro-phenyl)-1-(toluene-4-sulfonyl)-pyrrolidine.

16. A compound according to claim 2, (RS)-2-(3,4-difluoro-phenyl)-1-(toluene-4-sulfonyl)-pyrrolidine.

17. A compound according to claim 2, (RS)-2-(3-chloro-4-fluoro-phenyl)-1-(toluene-4-sulfonyl)-pyrrolidine.

18. A compound according to claim 2, (RS)-1-(4-fluoro-benzenesulfonyl)-2-(4-dimethylamino-3-chloro-phenyl)-pyrrolidine.

19. A compound according to claim 2, (RS)-1-(toluene-4-sulfonyl)-2-(4-trifluoromethyl-phenyl)-pyrrolidine.

20. A compound according to claim 2, (RS)-2-(4-chloro-3-methyl-phenyl)-1-(toluene-4-sulfonyl)-pyrrolidine.

21. A compound according to claim 2, (RS)-2-(4-fluoro-phenyl)-1-(4-trifluoromethyl-benzenesulfonyl)-pyrrolidine.

22. A compound according to claim 2, (RS)-2-(4-N,N-dimethylamino-phenyl)-1-(4-fluoro-benzenesulfonyl)-pyrrolidine.

23. A compound according to claim 2, (R)-1-(4-chloro-benzenesulfonyl)-2-(4-fluoro-phenyl)-pyrrolidine.

24. A compound according to claim 2, (S)-1-(4-chloro-benzenesulfonyl)-2-(4-fluoro-phenyl)-pyrrolidine.

25. A compound according to claim 2, (RS)-2-(4-ethyl-phenyl)-1-(toluene-4-sulfonyl)-pyrrolidine.

26. A compound according to claim 2, (RS)-2-(4-ethyl-phenyl)-1-(4-fluoro-benzenesulfonyl)-pyrrolidine.

27. A compound according to claim 2, (S)-2-(4-fluoro-phenyl)-1-(toluene-4-sulfonyl)-pyrrolidine.

28. A compound according to claim 2, (R)-2-(4-fluoro-phenyl)-1-(toluene-4-sulfonyl)-pyrrolidine.

29. A compound according to claim 2, (RS)-2-(4-fluoro-phenyl)-1-(4-methoxymethyl-benzenesulfonyl)-pyrrolidine.

30. A compound according to claim 2, (2RS,3RS)-2-(4-fluoro-phenyl)-3-methyl-1-(toluene-4-sulfonyl)-pyrrolidine.

31. A compound in accordance with claim 1, wherein
$R^1$ signifies hydrogen; and
$R^2$ signifies furyl, thienyl or pyridyl.

32. A compound according to claim 31, (RS)-1-(4-chloro-benzenesulfonyl)-2-thien-2-yl-pyrrolidine.

33. A compound according to claim 31, (RS)-2-thien-2-yl-1-(toluene-4-sulfonyl)-pyrrolidine.

34. A compound according to claim 31, (RS)-2-thien-3-yl-1-(toluene-4-sulfonyl)-pyrrolidine.

35. A compound according to claim 31, (RS)-2-furan-2-yl-1-(toluene-4-sulfonyl)-pyrrolidine.

36. A compound in accordance with claim 1, wherein
$R^1$ signifies hydrogen; and
$R^2$ signifies fluoro-phenyl.

37. A compound according to claim 36, (RS)-1-(4-chloro-benzenesulfonyl)-2-(4-fluorophenyl)-pyrrolidine.

38. A compound according to claim 36, (RS)-2-(4-fluoro-phenyl)-1-(toluene-4-sulfonyl)-pyrrolidine.

39. A compound according to claim 36, (S)-1-(4-chloro-benzenesulfonyl)-2-(4-fluoro-phenyl)-pyrrolidine.

40. A compound according to claim 36, (S)-2-(4-fluoro-phenyl)-1-(toluene-4-sulfonyl)-pyrrolidine.

41. A compound according to claim 36, (RS)-2-(4-fluoro-phenyl)-1-(4-methoxymethyl-benzenesulfonyl)-pyrrolidine.

42. A compound according to claim 36, (2RS,3RS)-2-(4-fluoro-phenyl)-3-methyl-1-(toluene-4-sulfonyl)-pyrrolidine.

43. A method of treating a disease related to metabotropic glutamate receptors in a mammal comprising administering to said mammal a compound of formula I in accordance with claim 1 and a pharmaceutically acceptable carrier in an amount which is effective in treating the disease related to the metabotropic glutamate receptor.

44. A pharmaceutical composition comprising a therapeutically effective amount of a compound of formula I in accordance with claim 1 and a pharmaceutically acceptable carrier.

* * * * *

UNITED STATES PATENT AND TRADEMARK OFFICE
CERTIFICATE OF CORRECTION

PATENT NO. : 6,284,785 B1
DATED : September 4, 2001
INVENTOR(S) : Vincent Mutel et al.

It is certified that error appears in the above-identified patent and that said Letters Patent is hereby corrected as shown below:

Title page,
Item [54], replace the present title with:
-- 1-ARENESULFONYL-2-ARYL-PYRROLIDINE AND PIPERIDINE DERIVATIVES. --

Signed and Sealed this

Ninth Day of April, 2002

Attest:

Attesting Officer

JAMES E. ROGAN
Director of the United States Patent and Trademark Office